(12) United States Patent
Milla et al.

(10) Patent No.: US 8,820,226 B2
(45) Date of Patent: *Sep. 2, 2014

(54) APPARATUS AND METHOD FOR SENSING THE CONCENTRATION OF PULP IN A CONCENTRATED PULP STREAM

(75) Inventors: Jose D. Milla, Lakeland, FL (US); Gregory W. Schrader, Lakeland, FL (US); Michael L. Suter, Lakeland, FL (US); David S. Danner, Land O Lakes, FL (US)

(73) Assignee: John Bean Technologies Corporation, Chicago, IL (US)

( * ) Notice: Subject to any disclaimer, the term of this patent is extended or adjusted under 35 U.S.C. 154(b) by 165 days.

This patent is subject to a terminal disclaimer.

(21) Appl. No.: 12/901,100

(22) Filed: Oct. 8, 2010

(65) Prior Publication Data

US 2012/0021102 A1   Jan. 26, 2012

Related U.S. Application Data

(63) Continuation-in-part of application No. 12/840,640, filed on Jul. 21, 2010.

(51) Int. Cl.
*A23L 2/06* (2006.01)
*A23L 2/08* (2006.01)
*G01F 1/00* (2006.01)
*G01N 9/26* (2006.01)

(52) U.S. Cl.
CPC ... *A23L 2/08* (2013.01); *G01F 1/00* (2013.01); *G01N 9/26* (2013.01)
USPC .................................. 99/486; 99/495; 99/510

(58) Field of Classification Search
USPC ......... 426/231, 232, 307, 321, 489, 495, 519, 426/521, 665; 99/486, 495, 510, 513; 73/73, 863.81

See application file for complete search history.

(56) References Cited

U.S. PATENT DOCUMENTS

| | | | | |
|---|---|---|---|---|
| 2,626,627 | A | * | 1/1953 | Jung et al. ....................... 137/88 |
| 3,898,124 | A | * | 8/1975 | Olson ............................ 162/238 |
| 3,952,577 | A | * | 4/1976 | Hayes et al. ................. 73/54.04 |
| 4,374,865 | A | | 2/1983 | Strobel ......................... 426/599 |
| 4,450,712 | A | * | 5/1984 | O'Shaughnessy ........... 73/61.78 |
| 4,463,025 | A | | 7/1984 | Strobel ......................... 426/599 |
| 4,569,853 | A | | 2/1986 | Strobel ......................... 426/599 |
| 5,260,086 | A | | 11/1993 | Downton et al. ............. 426/599 |
| 5,532,593 | A | * | 7/1996 | Maneval et al. .............. 324/306 |

(Continued)

OTHER PUBLICATIONS

IMPI Search Report mailed May 12, 2014, issued in corresponding Mexican Application No. MX/a/2013/000782, filed Jul. 19, 2011, 3 pages.

*Primary Examiner* — Thien S Tran
(74) *Attorney, Agent, or Firm* — Christensen O'Connor Johnson Kindness PLLC

(57) ABSTRACT

A juice processing system includes at least one fluid line for a concentrated pulp stream, and a flow restrictor coupled in fluid communication with the at least one fluid line for generating a pressure drop in the concentrated pulp stream indicative of a concentration of pulp therein. The system may further include at least one pressure sensor associated with the flow restrictor for sensing the pressure drop, and a controller coupled to the at least one pressure sensor for generating at least one control signal based upon the sensed pressure drop. The control signal may be for an upstream and/or a downstream control device.

20 Claims, 8 Drawing Sheets

(56) References Cited

U.S. PATENT DOCUMENTS

| | | | |
|---|---|---|---|
| 5,992,311 A | 11/1999 | Suter et al. | 100/37 |
| 6,375,996 B1 * | 4/2002 | Suter et al. | 426/231 |
| 6,906,172 B2 | 6/2005 | Bratcher et al. | |
| 2005/0086994 A1 * | 4/2005 | Silvis et al. | 73/1.16 |
| 2007/0006744 A1 * | 1/2007 | Gysling | 99/486 |
| 2008/0047973 A1 * | 2/2008 | Elsom et al. | 222/57 |
| 2008/0081094 A1 | 4/2008 | Yokoo et al. | 426/106 |

* cited by examiner

APPARATUS AND METHOD FOR SENSING THE CONCENTRATION OF PULP IN A CONCENTRATED PULP STREAM

RELATED APPLICATION

The present application is a continuation-in-part of U.S. patent application Ser. No. 12/840,640, filed on Jul. 21, 2010, the entire contents of which are incorporated by reference.

FIELD OF THE INVENTION

The invention relates to the field of fruit and vegetable processing, and more particularly, to a juice processing apparatus and method.

BACKGROUND OF THE INVENTION

The juice extraction process is known to those skilled in the art, such as described in U.S. Pat. No. 5,992,311, assigned to the present assignee, the disclosure of which is hereby incorporated by reference in its entirety. A fruit, vegetable and the like is fed to a juice extractor, which acts as the primary extractor, and produces a pure liquid (juice) and a fibrous material (pulp) from fruit, vegetables and the like.

After extraction, the mixture of juice and pulp is fed as a stream into a pulp concentrator, which is designed to separate a substantial amount of juice from the pulp and to adjust the concentration, or dryness, of the pulp to a desired range. The pulp concentrator may include a finisher, which may include a screw type finisher, paddle type finisher, centrifugal type finisher or decanter. The pulp concentrator may also include a rotary screen, vibrating screen or other type of separating device as readily appreciated by those skilled in the art.

The screw type and paddle type finishers, for example, rely on the juice to be extruded through a screen material, which regulates the size of the pulp that is maintained within the juice stream. Any pulp that is too large to be extruded through this screen is compressed by centrifugal and mechanical force, which is created by limiting the flow of pulp discharge either by a back pressure regulator and/or a weighted gate.

The juice that is separated from the pulp concentrator is further processed by pasteurization or evaporation as readily appreciated by those skilled in the art. The pulp that is separated from the pulp concentrator has various uses. In some juice processing facilities, this pulp is considered waste or is added to other fruit waste and processed into animal feed. In other juice processing facilities, this pulp is considered a valuable by-product and can either be used for pulpwash or collected as pulp cells. When used for pulpwash, the pulp is washed with water to recover juice solids, such as natural sugars, that are present in the pulp. When collected as pulp cells, the pulp from the concentrator is typically pasteurized to reduce the amount of natural occurring microorganisms prior to packaging, storage or use. Pulp cells may be added back to juice or used as an ingredient in other foods or beverages. When pasteurizing pulp, it may be critical to maintain the concentration, or density, of the pulp during pasteurization.

Problems arise, for example, when a pulp pasteurizer is fed with a concentration of pulp less than optimum. The energy for both heating and cooling is increased on a per ton basis of processed material discharged by the pulp pasteurizer in the form of packaged pulp material. Besides having a higher energy cost to produce the product, the final product can be out of density specification. This can result in a loss of product or an increase in reprocessing costs.

When the pulp density is below specification, there is an increase in the amount of carrier juice. Carrier juice is pasteurized along with the pulp and returned to the primary juice stream. Because it is pasteurized along with the pulp, it is often "overpasteurized" leading to quality and organoleptic degradation of the juice.

Should the concentration of pulp be too high, pressure limits within the pulp pasteurizer may be exceeded as well as proper feeding of the pulp pasteurizer can occur. Often this will create a blockage within the pulp pasteurizer and/or cause the temperatures within the pulp pasteurizer to fall out of specification preventing proper sterilization. This may result in either the loss of product or lower capacity.

Current methods to address these problems involve taking spot samples of the pulp discharge from the pulp concentrator and measuring the pulp concentration. Changes may then be made to the process to correct out of specification feed to the pulp pasteurizer.

One such measurement method is the grams/liter test, where a liter of pulp is mixed with a liter of water and put through a screening device to separate the water from the pulp. The remaining pulp on the screen is then weighed to determine the density.

Another measurement method is the quick fiber analysis, where dryness of the pulp is determined based on the free liquid that is removed without the application of pressure. For example, 200 grams of pulp sample are mixed with about 200 milliliters of water and stirred for a minute. This mixture sits for three minutes and is then stirred for another minute. The mixture is placed into a shaker with a 40 mesh screen for about three minutes and the liquid is retrieved from the sample. The liquid is measured in a graduated cylinder where the amount of liquid measured (in milliliters) is called the quick fiber. The total time is about 8-10 minutes, with even more time being needed for preparation.

As an alternative to the grams/liter test and the quick fiber analysis, pulp concentration may be measured using a nuclear magnetic resonance (NMR) sensor. U.S. Pat. No. 6,375,996, assigned to the present assignee, the disclosure of which is hereby incorporated by reference in its entirety, discloses obtaining a sample of the pulp, and measuring the pulp dryness using an NMR sensor.

Based on pulp concentrations in the sample measurements, manual adjustments may then be made to the pulp concentrator. In a screw type finisher, pulp concentration is changed by adjusting the finisher air pressure. In a paddle finisher, pulp concentration is changed by varying the speed of the paddle.

A disadvantage of performing the above described sample measurement approaches is that over time there may be wide variances in the pulp concentrations that can change even as pulp is being sampled and analyzed.

Maintaining the desired pulp concentration of juices packaged for retail consumption in the past has been a difficult and inaccurate process, because of the lack of a suitable on-line measurement and control system. However, a juice packaging company may wish to maintain a consistent pulp concentration in the retail packaged product for several reasons including: 1) maintaining a consistent consumer experience, 2) maintaining a consistent product visual appearance on the retail shelf, and 3) optimizing the process to reduce pulp use. Unfortunately, this has been difficult for several reasons including: 1) the pulp being added to the final product varies in concentration, 2) prior measurement techniques were not very accurate, and 3) prior measurement techniques required labor intensive and time consuming laboratory tests.

SUMMARY OF THE INVENTION

In view of the foregoing background, it is therefore an object of the present invention to sense pulp concentration accurately and in a continuous fashion, and implement one or more control operations based on the sensing.

These and other objects, features and advantages in accordance with the present invention are provided by a juice processing apparatus comprising at least one fluid line for a concentrated pulp stream, and a flow restrictor coupled in fluid communication with the at least one fluid line for generating a pressure drop in the concentrated pulp stream indicative of a concentration of pulp therein. The apparatus may also include at least one pressure sensor associated with the flow restrictor for sensing the pressure drop, and a controller coupled to the at least one pressure sensor for generating a control signal based upon the sensed pressure drop. Accordingly, the apparatus may advantageously provide the sensing of pulp concentration accurately and in a continuous fashion, and may implement one or more control operations based on the pulp concentration sensing.

In one group of embodiments, the apparatus may further include at least one upstream control device upstream of the flow restrictor and being responsive to the at least one control signal. In other words, in these embodiments, the controller generates an upstream control signal. In another group of embodiments, the apparatus may include at least one downstream control device downstream of the flow restrictor and being responsive to the at least one control signal. In these embodiments, the controller generates a downstream control signal.

For example, the at least one upstream control device may comprise a pulp concentrator. Accordingly, the controller is for controlling the pulp concentrator to maintain a pulp concentration within a predetermined range.

The at least one downstream control device may comprise a pulp metering device. Moreover, the apparatus may further include a juice supply and a juice metering device associated therewith, and a container filling station downstream from the pulp metering device and the juice volume metering device. The ratio of pulp and juice may be accurately controlled in the finished product within each container.

The flow restrictor may comprise a tube having an inlet and an outlet. In addition, the at least one pressure sensor may comprise an inlet pressure sensor associated with the inlet, and an outlet pressure sensor associated with the outlet.

In some embodiments, the at least one fluid line may comprise a primary fluid line and a secondary fluid line in parallel therewith. The primary and secondary fluid lines may both pass respective streams having the same pulp concentration. The second fluid line may carry a lower flow rate than the primary fluid line, or the secondary fluid line could carry the same or a higher flow rate. It may be desirable to have a constant flow rate in the secondary fluid line as the flow restrictor may be coupled in fluid communication with the secondary fluid line. In addition, the control signal may be for at least one control device operating on the primary fluid line.

The juice processing apparatus may further comprise at least one flow rate sensor coupled in fluid communication with the at least one fluid line. In addition, the apparatus may also include at least one fluid pump coupled in fluid communication with the at least one fluid line.

In accordance with another aspect, the juice processing apparatus may include a juice supply, a pulp supply, and a container filling station downstream from the juice and pulp supplies and permitting control of a ratio of juice and pulp. In this embodiment, the apparatus may also include a flow restrictor for generating a pressure drop in a concentrated pulp stream associated with the pulp supply, and at least one pressure sensor associated with the flow restrictor for sensing the pressure drop. In addition, the apparatus may also include a controller coupled to the at least one pressure sensor and the container filling station to control the ratio of juice and pulp.

A method aspect is for juice processing comprising generating a pressure drop in a concentrated pulp stream indicative of a concentration of pulp therein, sensing the pressure drop, and generating at least one control signal based upon the sensed pressure drop. Generating the at least one control signal may comprise generating at least one upstream control signal for an upstream control device, for example. Alternately or additionally, generating the at least one control signal may comprise generating at least one downstream control signal for an upstream control device.

Another juice processing method includes using a flow restrictor for generating a pressure drop in a concentrated pulp stream associated with a pulp supply, and using at least one pressure sensor associated with the flow restrictor for sensing the pressure drop. The method may further include filling a plurality of containers downstream from a juice supply and the pulp supply while controlling a ratio of juice and pulp based upon the sensed pressure drop.

DETAILED DESCRIPTION OF THE PREFERRED EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout, and prime and multiple prime notation are used to indicate similar elements in alternative embodiments.

Figure 1:
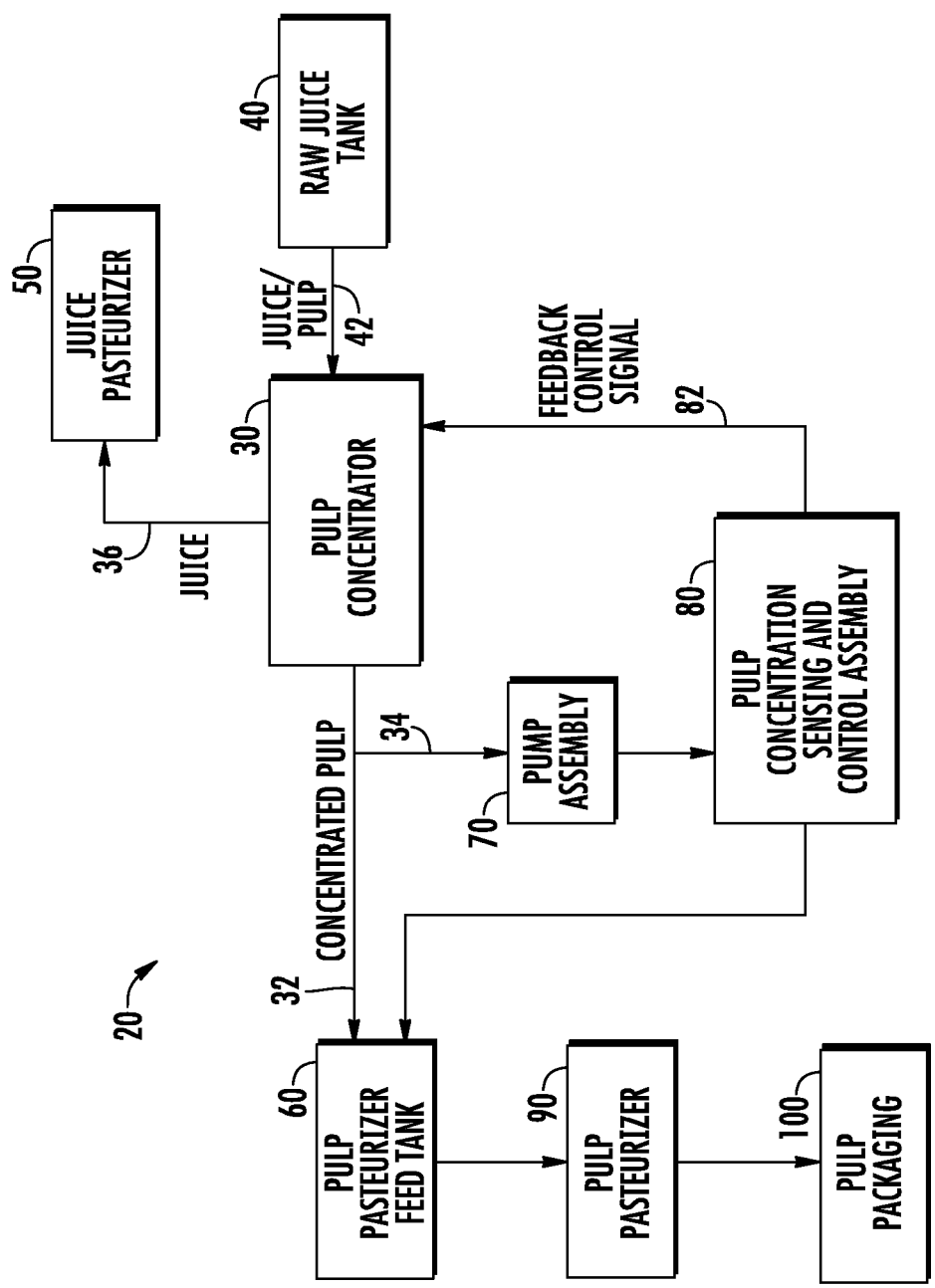
FIG. 1 is a block diagram of a juice processing apparatus in accordance with the present invention.

Referring initially to FIG. 1, a juice processing apparatus 20 includes a pulp concentrator 30 that is fed from a raw juice tank 40. The pulp concentrator 30 is also known as a finisher, which may include either a screw type finisher and/or a paddle finisher. The raw juice tank 40 provides a stream 42 of liquid juice and pulp to the pulp concentrator 30. Although not illustrated, an extractor is used to feed the raw juice tank 40 by extracting the liquid juice and pulp from fruit, such as an orange, or a vegetable.

The pulp concentrator 30 generates a primary concentrated pulp stream 32, a secondary concentrated pulp stream 34, and a juice stream 36. The juice stream 36 is fed to a juice pasteurizer 50. The primary concentrated pulp stream 32 is fed to a pulp pasteurizer feed tank 60. The secondary concentrated pulp stream 34 is fed to a pump assembly 70 and a pulp concentration sensing and control assembly 80 before being also fed to the pulp pasteurizer feed tank 60.

As will be discussed in greater detail below, the pump assembly 70 and the pulp concentration sensing and control assembly 80 advantageously allow for a continuous sensing of the pulp concentration of the secondary concentrated pulp stream 34 as it is discharged from the pulp concentrator 30.

The primary concentrated pulp stream 32 and the secondary concentrated pulp stream 34 both have the same pulp concentration. The primary concentrated pulp stream 32 may have a higher flow rate than the secondary concentrated pulp stream 34. The secondary concentrated pulp stream 34 may be referred to as a slip stream sample of the primary concentrated pulp stream 32. The primary and secondary concentrated pulp streams 32, 34 are typically measured in gallons/minute.

Feedback information from the pulp concentration sensing and control assembly 80 is provided to the pulp concentrator 30. Based on measured variations of the pulp concentration within the secondary concentrated pulp stream 34, the pulp concentration sensing and control assembly 80 automatically provides a varying feedback output signal 82 to the pulp concentrator 30 so that a desired pulp concentration, typically in grams per liter, can be maintained regardless of upstream process variations which might otherwise cause wide variations in pulp density discharged by the pulp concentrator 30. The pulp concentration sensing and control assembly 80 enables the user to define a desired pulp concentration which maximizes production, and prevents process upsets within the downstream pulp pasteurizer 90 being fed by the pulp pasteurizer feed tank 60.

The pulp concentration sensing and control assembly 80 compares the desired set point to that of the measured value and provides the feedback control signal 82 to the pulp concentrator 30 to increase or decrease the density of the discharged pulp stream. For example, if the pulp concentrator 30 includes a screw type finisher, pulp concentration is changed by adjusting the finisher air pressure as readily understood by those skilled in the art. Similarly, if the pulp concentrator 30 includes a paddle finisher, pulp concentration is changed by varying the speed of the paddle as also readily understood by those skilled in the art.

In the event that the pulp concentration sensing and control assembly 80 cannot produce the desired concentration of pulp, preset alarms are generated allowing the user to take immediate steps to correct the situation prior to producing either a failure within the pulp pasteurizer 90, such as plugging, or the production of an out-of-specification product at the pulp packaging 100 downstream from the pulp pasteurizer 90.

An additional feature is to allow for the user to acquire information via a network connection as to the concentration of pulp which has been fed to the pulp pasteurizer 90. In the cases where no additional juice is separated prior to packaging, this information provides for validation and documentation of the pulp density at the pulp packaging 100.

Figure 2:
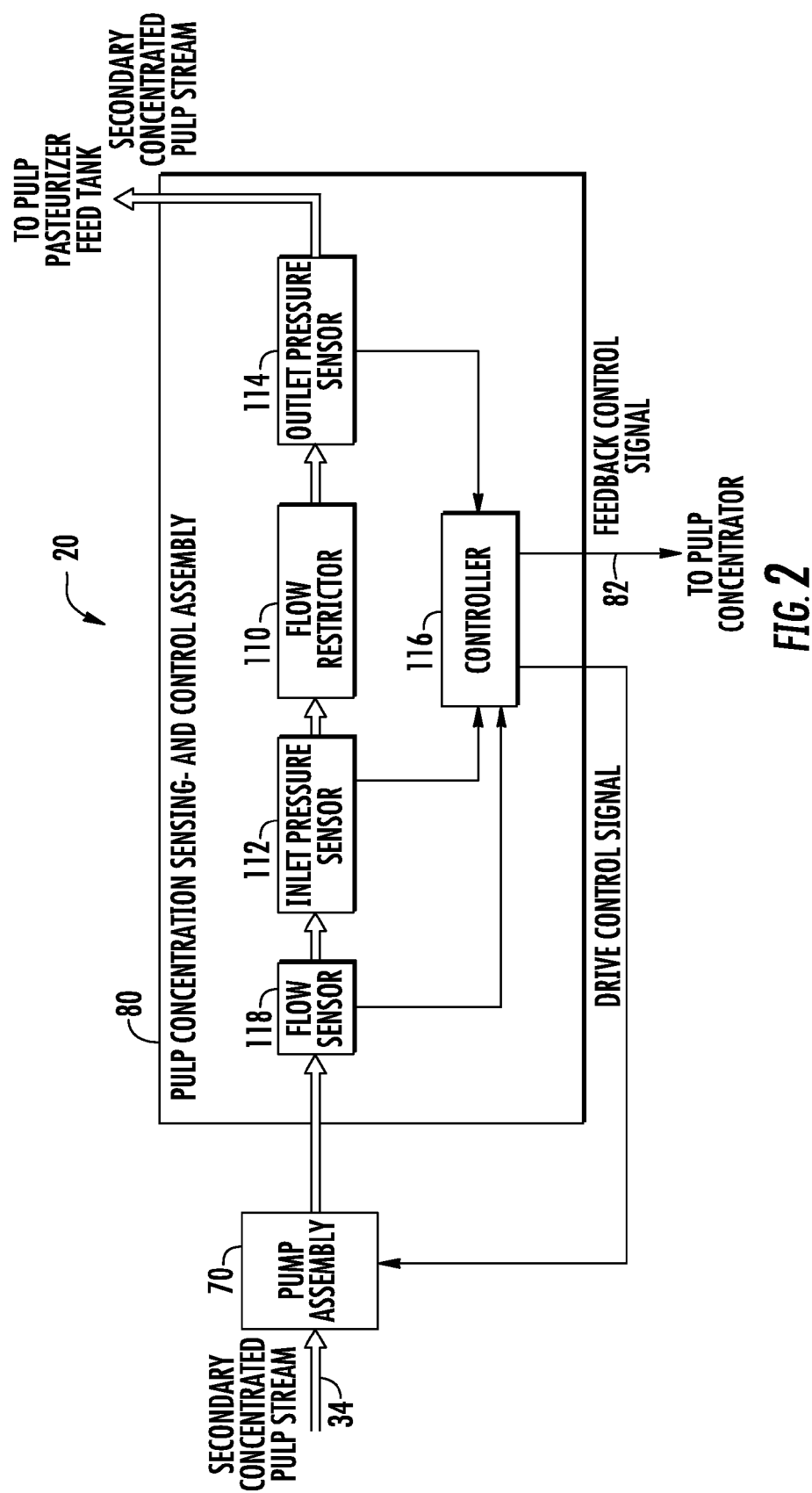
FIG. 2 is a detailed block diagram of the pulp concentration sensing and control assembly shown in FIG. 1.

Referring now to FIG. 2, the pulp concentration sensing and control assembly 80 will now be discussed in greater detail. In addition, the pump assembly 70 will also be discussed in greater detail since it is necessary for the pump assembly 70 to provide the secondary concentrated pulp stream 34 to the pulp concentration sensing and control assembly 80 at a predetermined flow rate.

The pump assembly 70 comprises a positive displacement pump designed to provide a minimum of shear to the pulp as possible. A typical style for this pump would be a progressive cavity pump.

The pulp concentration sensing and control assembly 80 includes a flow restrictor 110 coupled in the secondary concentrated pulp stream 34 for generating a pressure drop therein, with the pressure drop being indicative of a concentration of pulp in the secondary concentrated pulp stream 34.

As discussed above, the concentration of pulp in the secondary concentrated pulp stream 34 is equal to the concentration of pulp in the primary concentrated pulp stream 32. Pressure sensors 112, 114 are associated with the flow restrictor 110 for sensing the pressure drop. A controller 116 is for controlling the pulp concentrator 30 based upon the sensed pressure drop.

For the pulp concentration sensing and control assembly 80 to operate correctly the pump assembly 70 needs to provide a stream of pulp at a consistent flow rate. In other words, control of the rate at which the secondary concentrated pulp stream 34 is fed into the flow restrictor 110 is important to sensing and controlling the pulp concentration. This control is provided using a flow rate sensor 118 in the secondary concentrated pulp stream 34.

The flow rate sensor 118 provides a flow rate signal to the controller 116 corresponding to the measured flow rate of the secondary concentrated pulp stream 34. In response, the controller 116 generates a drive control signal for a variable speed drive that controls an electrical motor associated with the pump assembly 70, thus maintaining the desired flow rate to the flow restrictor 110. This is necessary for proper sensing of the pulp density in the secondary concentrated pulp stream 34.

The flow restrictor 110 may comprise a tube or venturi tube, for example. The tube 110 has an inlet and an outlet. The length and diameter of the tube 110 is selected to correspond to a consistent and desired pressure drop. In other words, the diameter of the tube 110 is less than the diameter of the pipe feeding the secondary concentrated pulp stream 34 thereto. For example, the diameter of the tube 110 may be within a range of ¼ to ½ inches outside diameter, whereas the diameter of the pipe feeding the secondary concentrated pulp stream 34 thereto may be within a range of 1 to 2 inches outside diameter. The length of the tube 110 may also vary, but a typical length may be within a range of about 6 to 18 inches, for example. Other lengths and diameters may be used as long as a consistent and desired pressure drop is maintained across the tube 110.

The desired pressure drop across the tube 110 is based on the characteristics of pulp at the desired concentration range of the downstream pulp pasteurizer 90. The inlet pressure sensor 112 is associated with the inlet of the tube 110, and measures the pressure prior to entering the flow restrictor. The outlet pressure sensor 114 is associated with the outlet of the tube 110, and measures the pressure exiting the flow restrictor. The outlet pressure sensor 114 is intended to isolate the effects of pressure losses created by the pulpy stream as it exits the flow restrictor.

The controller 116 receives pressure signals from the inlet and outlet pressure sensors 112, 114. The controller 116 executes an algorithm that incorporates the known characteristic of the flow restrictor 110 as it reacts (i.e., pressure drop) to variances of pulp concentration and the flow rate of the secondary concentrated pulp stream 34 provided thereto.

The algorithm calculates the pulp concentration and produces and averages this over time, and then generates the feedback control signal 82 for control of the pulp concentrator 30 based on the average measured values and the desired pulp concentration as set by the user. The feedback control signal 82 is not limited to a single signal, but could include two or more signals.

Figure 3:
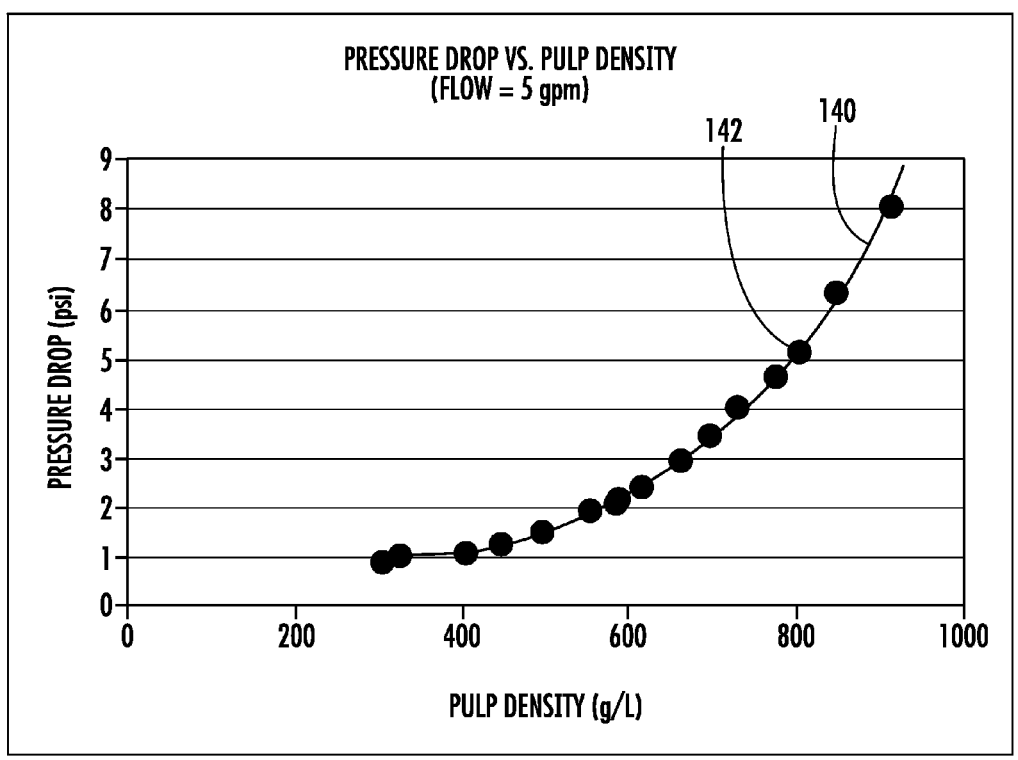
FIG. 3 is a graph illustrating pressure drop versus pulp density in accordance with the present invention.

As illustrated in FIG. 3, pressure drop versus pulp density is plotted along line 140 for a uniform flow rate through the flow restrictor 110. The horizontal axis is the pulp density in grams per liter (g/l), and the vertical axis is pressure drop in pounds per square inch (psi). The flow rate of the secondary concentrated pulp stream 34 received by the flow restrictor 110 is 5 gallons per minute (gpm).

For example, a pressure drop of 5 psi corresponds to a pulp concentration of 800 g/l for a flow rate of 5 gpm, as indicated by point 142. Test data will vary based on the size (length and diameter) of the flow restrictor 100, and the flow rate of the secondary concentrated pulp stream 34, as readily appreciated by those skilled in the art.

The pulp concentration at the output of the pulp concentrator 30 may thus be determined by comparing the pressure drop at a given flow rate across the flow restrictor 110 to previously collected empirical data, such as shown in FIG. 3. The controller 116 also includes a user interface that allows the user to input a pulp concentration set point. This set point may be entered locally at the user interface or remotely via network connection.

To maintain pulp concentration from the pulp concentrator 30 within a narrow user-defined band, the controller 116 may compare the measured pressure drop across the flow restrictor 110 to the set point from the user interface. For example, the set point may be entered as a unit of pressure drop, such as in pounds per square inch; or may be a unit of pulp density, such as in grams per liter; or may be a unitless number that correlates to pulp density. If the set point is entered as a unit of pulp density, the controller 116 may convert the pulp density set point to a pressure drop set point based on previously collected empirical data. If the measured pressure drop across the controller 116 is different than the user-defined set point, the controller will send a signal to the pulp concentrator 30 to either increase or decrease pulp density. The controller 116 may contain an algorithm to control pulp concentration versus a desired set point. The controller 116 may also provide an alarm if the measured pulp density deviates from the set point, or if the controller 116 is not able to achieve the set concentration within a given period of time. The controller 116 may also record historical set points and measured pulp density data to allow the user to review historical performance.

Figure 4:
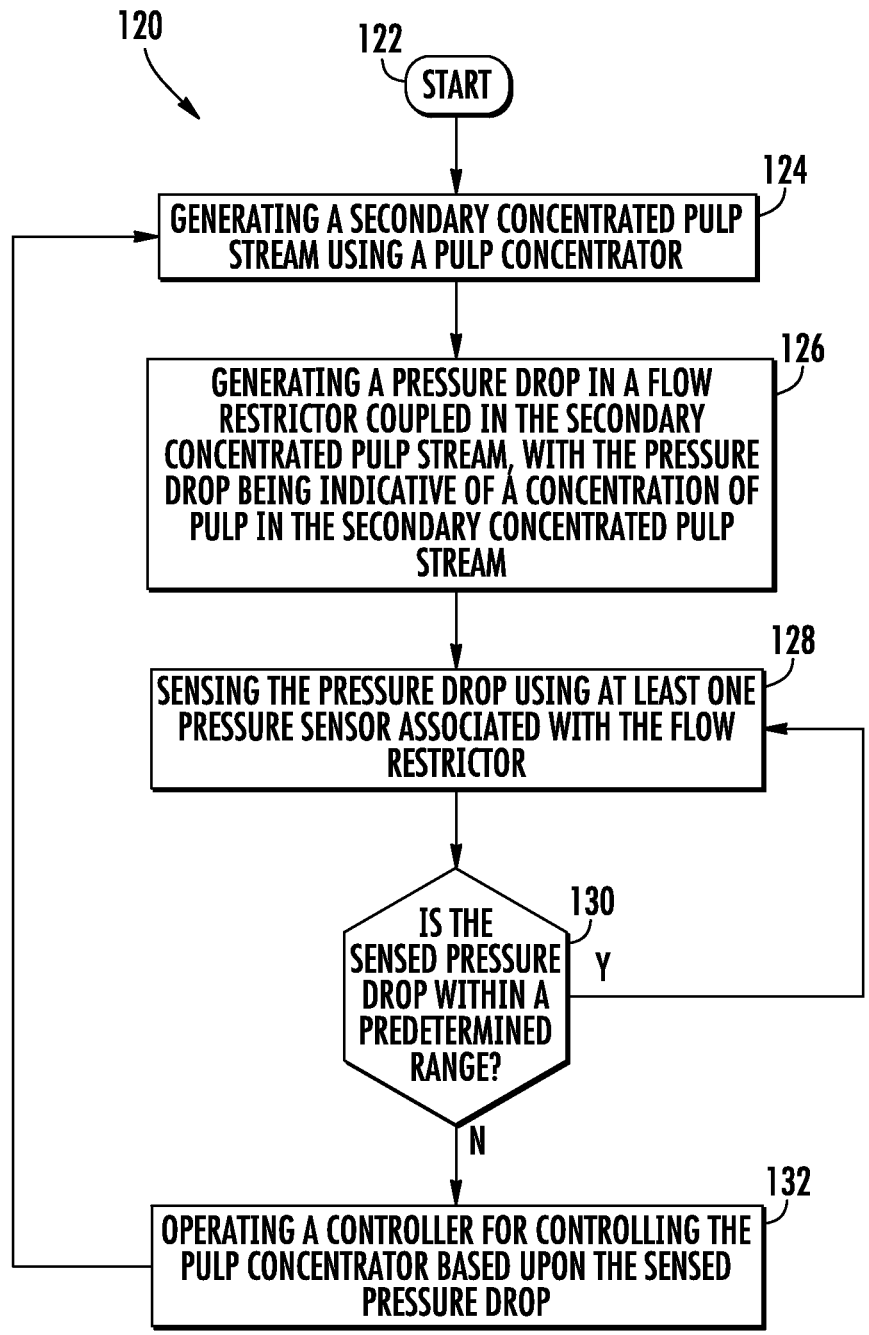
FIG. 4 is a flowchart illustrating a method for sensing and controlling pulp concentration for a juice processing apparatus in accordance with the present invention.

Another aspect is directed to a method for sensing and controlling pulp concentration for a juice processing apparatus 20 as described above. Referring now to the flowchart 120 in FIG. 4, from the start (Block 122), the method comprises generating a secondary concentrated pulp stream 34 using a pulp concentrator 30 at Block 124. At Block 126, a pressure drop is generated in a flow restrictor 110 coupled in the secondary concentrated pulp stream 34. The pressure drop is indicative of a concentration of pulp in the secondary concentrated pulp stream 34. The pressure drop is sensed using at least one pressure sensor 112, 114 associated with the flow restrictor 110 at Block 128. At decision block 130, the sensed pressure drop is compared to a predetermined range. If the sensed pressure drop is within the predetermined range, then the pressure drop is continued to be sensed at Block 128. However, if the sensed pressure drop is not within the predetermined range, then the method comprises operating a controller 116 at Block 132 for controlling the pulp concentrator 30 based upon the sensed pressure drop at Block 128. The controller generates a feedback control signal 82 for the pulp concentrator.

Figure 5:
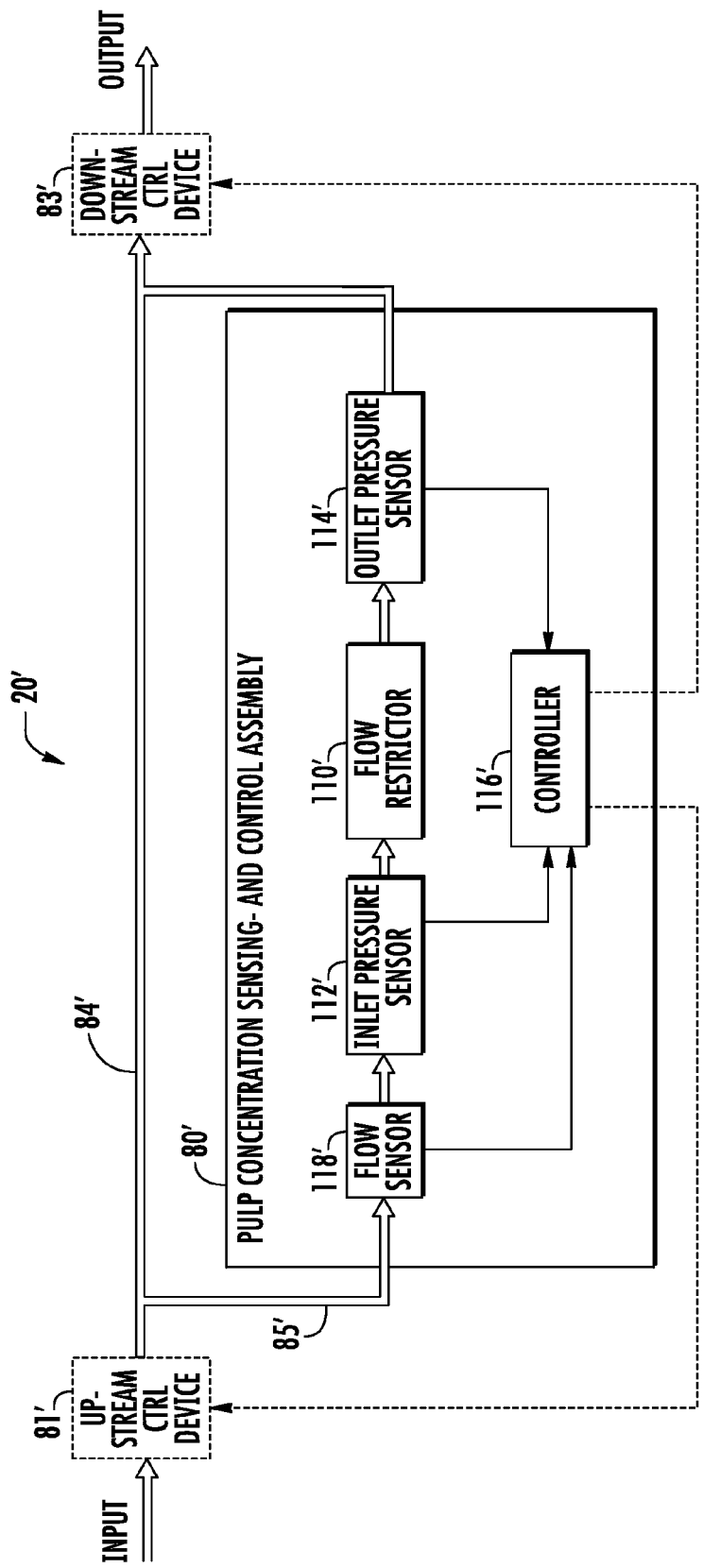
FIG. 5 is a block diagram of another embodiment of a juice processing apparatus in accordance with the present invention.

Referring now additionally to FIG. 5 another juice processing apparatus 20' is now described. In this embodiment, the apparatus 20' includes the pulp concentration and control assembly 80', and its associated components as described above, but also illustratively includes an optional upstream control device 81' as well as an optional downstream control device 83'. In other words, the controller 116' may process the pulp concentration data and calculate an adjustment for upstream and/or downstream processing as will be appreciated by those skilled in the art.

The controller 116' may generate an upstream control signal that is passed to the upstream control device 81' and/or may generate a downstream control signal that is passed to the downstream control device 83'. In the embodiment of the apparatus 20 described above with reference to FIG. 1, the upstream control device is in the form of the pulp concentrator 30. Of course, the controller 116' may generate the signals that are, in turn, used by other intervening control circuitry as will also be understood by those skilled in the art.

In this embodiment, the apparatus 20' includes a primary concentrated pulp stream passing through a primary fluid line 84' and a secondary concentrated pulp stream passing through a secondary fluid line 85' between the input and output. The primary fluid line 84' and the secondary fluid line 85' are in parallel. The primary and secondary fluid lines 84', 85' are both passing respective streams having the same pulp concentration. The secondary fluid line 85' may carry a lower flow rate than the primary fluid line 84'. Of course, the secondary fluid line 85' could also carry a higher flow rate or the same flow rate in other embodiments. As will be appreciated by those skilled in the art, it may be desirable to maintain a constant flow rate in the secondary fluid line 85'. In addition, the flow restrictor 110' is coupled in fluid communication with the secondary fluid line 85'. In other words the pulp concentration sensing and control assembly 80' is connected in fluid communication with the secondary fluid or sample line 85'. The other components of the juice processing apparatus 20' not specifically discussed are similar to those components already discussed above, and need no further discussion.

Figure 6:
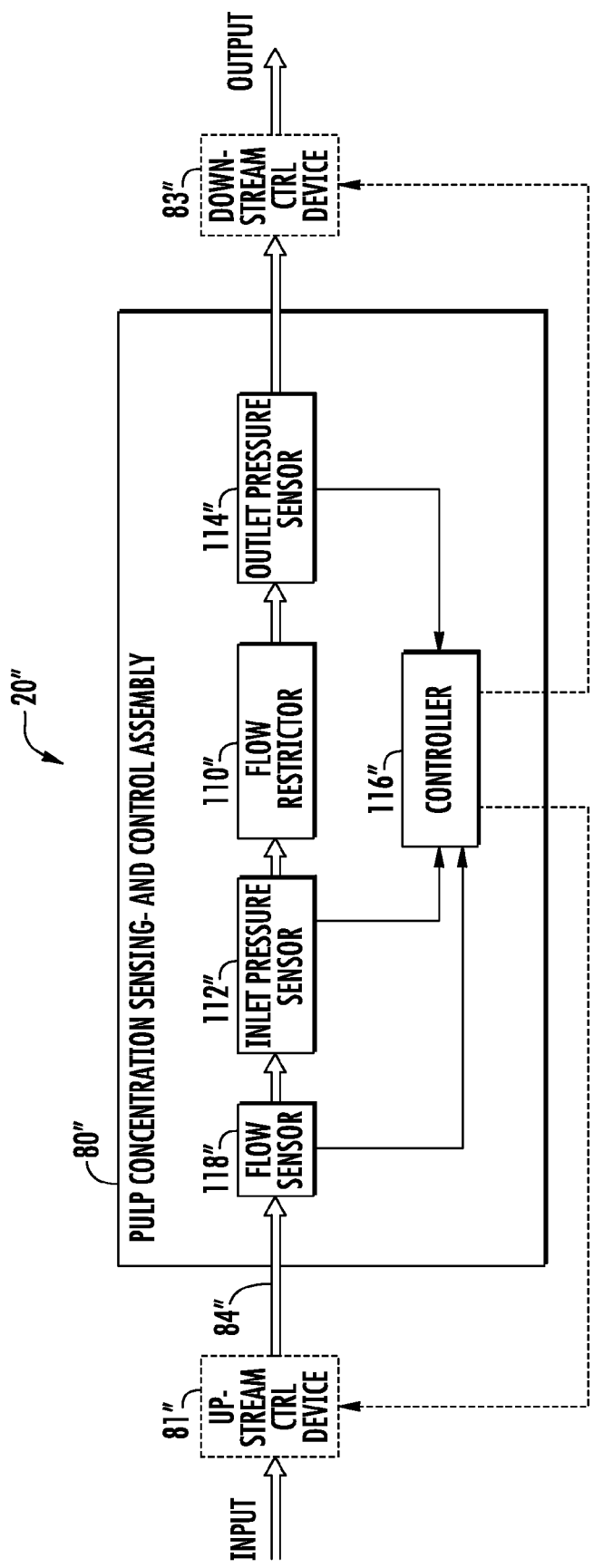
FIG. 6 is a block diagram of yet another embodiment of a juice processing apparatus in accordance with the present invention.

Referring now additionally to FIG. 6, another embodiment of a juice processing apparatus 20" is now described. In this embodiment, the pulp concentration sensing and control assembly 80" is coupled in fluid communication with the primary fluid line 84". The upstream control device 81" and the downstream control device 83" are coupled in fluid communication with the primary fluid line 84". Of course, in some embodiments only one of the upstream and downstream control devices 81", 83" may be used. The other components of the juice processing apparatus 20" not specifically discussed are similar to those components already discussed above, and need no further discussion.

Figure 7:
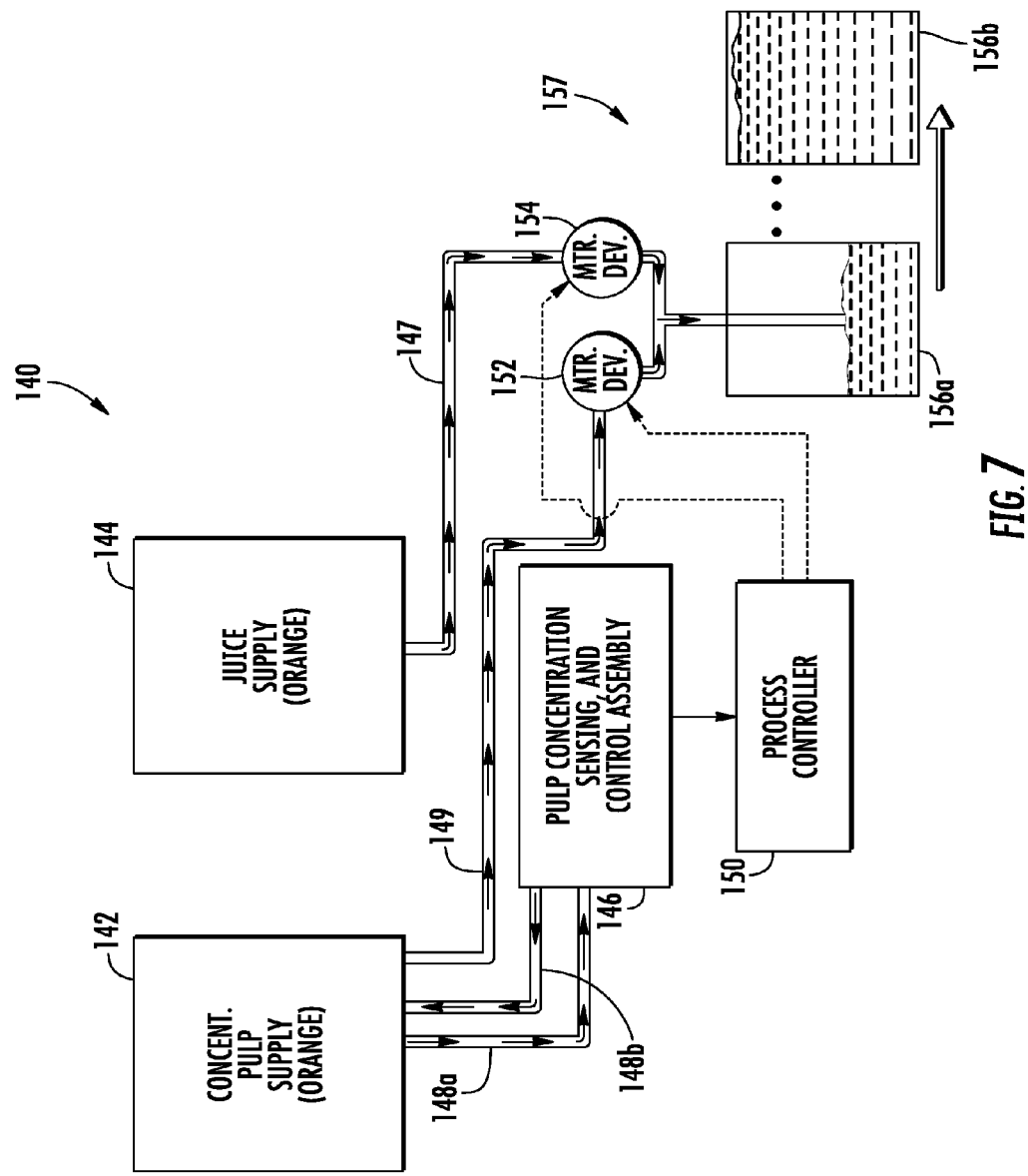
FIG. 7 is a block diagram of a juice processing apparatus including a container filler in accordance with the present invention.

Turning now to FIG. 7, an exemplary juice processing apparatus 140 using what may also be considered as a downstream control device in the form of a pulp metering device 152 is now described. The pulp metering device 152 may be a volume or flow rate metering device as will be appreciated by those skilled in the art. The apparatus 140 includes a pulp supply 142 of concentrated orange pulp and an associated pulp metering device 152, and a juice supply 144 of orange juice and an associated juice (volume or flow rate) metering device 154 coupled to the juice supply via fluid line 147. A plurality of containers 156a-156n are advanced at a container filling station 157 past the pulp and juice metering devices 152, 154 by a conveyor, not shown, as will be appreciated by those skilled in the art. The apparatus 140 also includes a pulp concentration sensing and control assembly 146 including the flow restrictor, and associated at least one pressure sensor, coupled in fluid communication between the pulp supply 142 and its associated metering device 152. In other words, the pulp concentration sensing and control assembly 146 may include the same components as the corresponding assemblies 80, 80', and 80" described above.

In the illustrated embodiment of the juice processing apparatus 140, an overall process controller 150 is schematically illustrated and coupled between the pulp concentration sensing and control assembly and the pulp volume device 152. The process controller 150 may also be operatively connected to the juice metering device 154 as well as other control devices, not shown for brevity and clarity of explanation. In other embodiments, the process controller 150 may not be needed, with instead the output of the pulp concentration sensing and control assembly 146 being directly coupled to the pulp metering device 152. Of course in yet other embodiments, the pressure sensor and pulp concentration calculations may be performed entirely in the process controller 150 as will be appreciated by those skilled in the art.

In slightly different terms, the juice processing apparatus 140 includes a juice supply 142, a pulp supply 144, and a container filling station 157 downstream from the juice and pulp supplies and permitting control of a ratio of juice and pulp. The flow restrictor within the pulp concentration sensing and control assembly 146 generates a pressure drop in a concentrated pulp stream associated with the pulp supply, and the at least one pressure sensor associated with the flow restrictor senses the pressure drop. In this embodiment, the concentrated pulp stream is recirculated using a pump, not shown, via secondary fluid lines 148a,148b from the pulp supply 142. And the concentrated pulp from the pulp supply 142 is also delivered via the primary fluid line 149 to the filling station 157. The controller within the pulp concentration sensing and control assembly 146 is coupled to the at least one pressure sensor and the container filling station 157 (via the optional process controller 150) to control the ratio of juice and pulp as will be appreciated by those skilled in the art.

Figure 8:
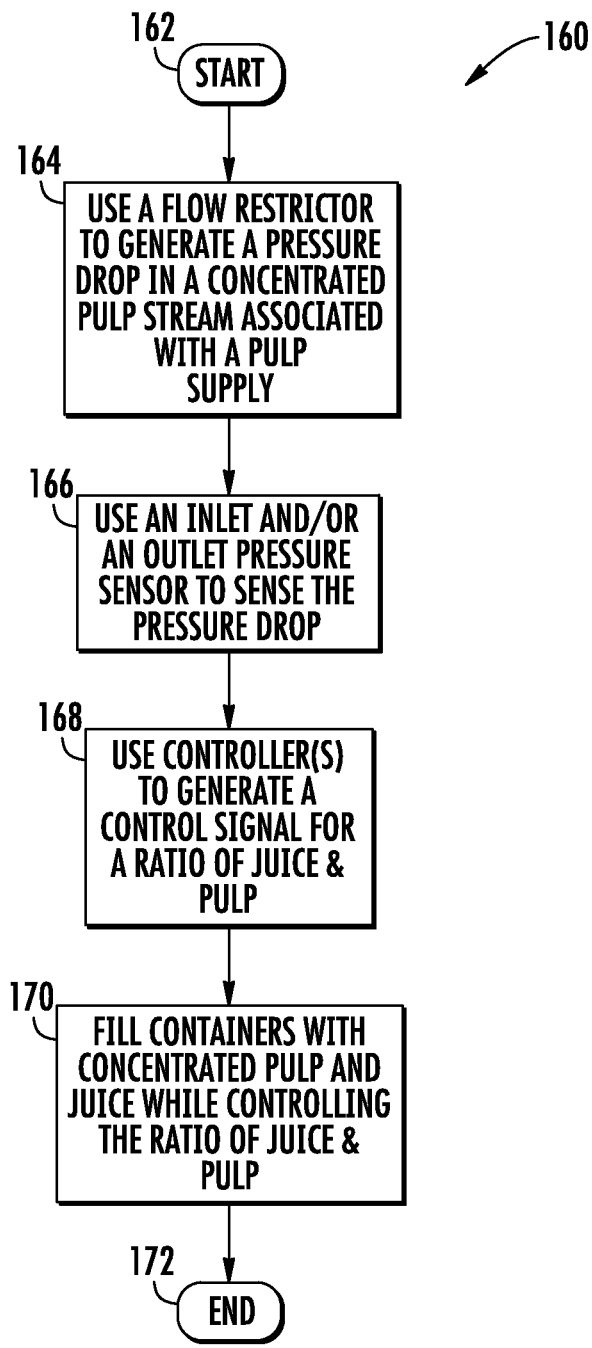
FIG. 8 is a flowchart illustrating the method for filling containers in accordance with the present invention.

Turning now additionally to the flowchart 160 of FIG. 8, a method aspect is described related to the juice processing apparatus 140 shown in FIG. 7. From the start (Block 162), the method includes the use of a flow restrictor to generate a pressure drop in a concentrated pulp stream associated with a pulp supply 142. Next an inlet and/or an outlet pressure sensor are used to sense the pressure drop in the flow restrictor at Block 166. At Block 168 one or more controllers 146, 150 are used to generate a control signal for a ratio of pulp and juice. The containers 156a-156n are filled at Block 170 based upon the control signal for the ratio of juice and pulp, before ending (Block 172).

Again, in slightly different terms, this juice processing method includes using a flow restrictor for generating a pressure drop in a concentrated pulp stream associated with a pulp supply, and using at least one pressure sensor associated with the flow restrictor for sensing the pressure drop. The method may further include filling a plurality of containers downstream from a juice supply and the pulp supply while controlling a ratio of juice and pulp based upon the sensed pressure drop.

Typically, concentrated pulp (300-1000 g/l) is injected into a juice stream as the juice is transported to the packaging equipment or in the filler. The rate of pulp injection may be controlled by a ratio of volumetric flow rates of the juice and pulp streams. The accuracy of the pulp concentration in the final product relies on the accurate knowledge of the pulp concentration being injected and the accuracy of the test to determine the final pulp concentration. Prior existing methods to measure the pulp concentration involved screening the pulp and determining the weight fraction of the pulp in the sample. The inherent error in these screen methods was sometimes greater than the desired pulp concentration. Periodic corrections were made to the pulp injection rate based on the data obtained from the laboratory screen tests. The processing apparatus 140 including the pulp concentration sensing and control assembly 146 in accordance with the disclosed embodiments overcomes these difficulties of the prior art as will be appreciated by those skilled in the art.

Filling of liquid food products into consumer containers is well known in the art. Food product may be filled aseptically or non-aseptically into containers and several companies manufacture various styles of filling equipment. These companies include JBT Corporation of Chicago, Ill.; Tetra Pak of Vernon Hills, Ill, Krones AG of Neutraubling, Germany; GEA Group of Bochum, Germany; and others. In this equipment, food product is filled into each container by either weight or volumetric control. For liquid food products, filling is primarily done through volumetric control. When filling two-component food products, for example, juice and pulp, it is typically desirable to maintain the same ratio of the two components in each package. As will be appreciated by those skilled in the art, there are at least three ways to accomplish this:

1. Batch mix the two components in a holding container and then filling the containers from the mixed batch. The challenge of this method is keeping the entire batch consistent during the filling operation. This can be a problem when the two components have differing densities. This may be partially overcome through efficient mixing. In accordance with the disclosed embodiments, it can be determined how much total pulp is mixed into the batch based on the measured density of the pulp.

2. Inline mixing of the two components prior to the filling machine. In this approach, the two components are metered together and mixed inline prior to filling. The two components can be metered by measuring the flow rate of each component (with a flowmeter, for example) and adjusting the flow rate of either component by changing the speed of a pump (such as a positive displacement pump, for example). The accuracy of this method requires the accurate knowledge of the pulp density to maintain a constant amount of pulp in each container. If the density is known, than the ratio of the two components may be controlled in one of two ways:

a. Keeping the flow of the juice portion constant and varying the injection of the pulp portion based on knowledge of the pulp density as discussed herein.

b. Keeping the flow of the pulp portion constant and varying the flow rate of the juice portion in order to control the ratio of the two parts.

3. A third way of accomplishing a constant ratio of the two components, is to fill each component into the container individually or in separate steps. In this approach, one component (pulp, for example) is metered into each container by one filling head or device, and the second component (juice for example) is fed into each container by a separate, consecutive filling device. For example, one station of the filling head may meter 30 ml of pulp into a container, and a consecutive filling head or consecutive filling machine may meter 1 L of juice into the container. The amount of the pulp that is placed into each container may be adjusted by the downstream feedback of the pulp density device.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A juice processing apparatus comprising:
   at least one fluid line for a concentrated fruit or vegetable pulp stream;
   a flow restrictor coupled in fluid communication with said at least one fluid line for generating a pressure drop in the concentrated fruit or vegetable pulp stream indicative of a concentration of fruit or vegetable pulp therein, said flow restrictor comprising a tube having an inlet and an outlet;
   at least one pressure sensor coupled to said flow restrictor for sensing the pressure drop, said at least one pressure sensor comprising an inlet pressure sensor coupled to the inlet; and
   a controller coupled to said at least one pressure sensor for generating at least one control signal based upon the sensed pressure drop.

2. The juice processing apparatus according to claim 1 further comprising at least one upstream control device upstream of said flow restrictor and being responsive to the at least one control signal.

3. The juice processing apparatus according to claim 2 wherein said at least one upstream control device comprises a fruit or vegetable pulp concentrator.

4. The juice processing apparatus according to claim 3 wherein said controller is for controlling said fruit or vegetable pulp concentrator to maintain a fruit or vegetable pulp concentration within a predetermined range.

5. The juice processing apparatus according to claim 1 further comprising at least one downstream control device downstream of said flow restrictor and being responsive to the at least one control signal.

6. The juice processing apparatus according to claim 5 wherein said at least one downstream control device comprises a fruit or vegetable pulp metering device.

7. The juice processing apparatus according to claim 6 further comprising a container filling station downstream from said fruit or vegetable pulp metering device.

8. The juice processing apparatus according to claim 7 further comprising a juice supply and a juice metering device associated therewith upstream from said container filling station.

9. The juice processing apparatus according to claim 1 wherein said at least one pressure sensor further comprises an outlet pressure sensor coupled to the outlet.

10. The juice processing apparatus according to claim 1 wherein said at least one fluid line comprises a primary fluid line and a secondary fluid line in parallel therewith; and wherein said flow restrictor is coupled in fluid communication with said secondary fluid line.

11. The juice processing apparatus according to claim 1 further comprising at least one flow rate sensor coupled in fluid communication with said at least one fluid line.

12. The juice processing apparatus according to claim 1 further comprising at least one fluid pump coupled in fluid communication with said at least one fluid line.

13. A fruit or vegetable pulp concentration sensing and control assembly for a juice processing apparatus including at least one fluid line for a concentrated fruit or vegetable pulp stream, the fruit or vegetable pulp concentration sensing and control assembly comprising:
   a flow restrictor to be coupled in fluid communication with the at least one fluid line for generating a pressure drop in the concentrated fruit or vegetable pulp stream indicative of a concentration of fruit or vegetable pulp therein, said flow restrictor comprising a tube having an inlet and an outlet;
   at least one pressure sensor coupled to said flow restrictor for sensing the pressure drop, said at least one pressure sensor comprising an inlet pressure sensor coupled to the inlet; and
   a controller coupled to said at least one pressure sensor for generating at least one control signal based upon the sensed pressure drop.

14. The fruit or vegetable pulp concentration sensing and control assembly according to claim 13 wherein the at least one control signal comprises an upstream control signal for an upstream control device upstream of said flow restrictor.

15. The fruit or vegetable pulp concentration sensing and control assembly according to claim 13 wherein the at least one control signal comprises a downstream control signal for at least one downstream control device downstream of said flow restrictor.

16. The fruit or vegetable pulp concentration sensing and control assembly according to claim 13 wherein said at least one pressure sensor further comprises an outlet pressure sensor coupled to the outlet.

17. A juice processing apparatus comprising:
   a juice supply;
   a fruit or vegetable pulp supply;
   a container filling station downstream from said juice and fruit or vegetable pulp supplies and permitting control of a ratio of juice and fruit or vegetable pulp;
   a flow restrictor for generating a pressure drop in a concentrated fruit or vegetable pulp stream coupled to said fruit or vegetable pulp supply, said flow restrictor comprising a tube having an inlet and an outlet;
   at least one pressure sensor coupled to said flow restrictor for sensing the pressure drop, said at least one pressure sensor comprising an inlet pressure sensor coupled to the inlet; and
   a controller coupled to said at least one pressure sensor and said container filling station to control the ratio of juice and fruit or vegetable pulp.

18. The juice processing apparatus according to claim 17 wherein said at least one pressure sensor further comprises an outlet pressure sensor coupled to the outlet.

19. The juice processing apparatus according to claim 17 wherein said container filling station comprises a juice metering device coupled to said juice supply.

20. The juice processing apparatus according to claim 17 wherein said container filling station comprises a fruit or vegetable pulp metering device coupled to said pulp supply.

* * * * *